US006254871B1

(12) United States Patent
Ohnishi

(10) Patent No.: US 6,254,871 B1
(45) Date of Patent: Jul. 3, 2001

(54) THERAPEUTIC USES OF SPECIALLY PROCESSED GARLIC FOR SICKLE CELL DISEASE

(75) Inventor: Tsuyoshi Ohnishi, King of Prussia, PA (US)

(73) Assignee: Wakunaga of America Co., Ltd., Mission Viejo, CA (US)

( * ) Notice: Subject to any disclaimer, the term of this patent is extended or adjusted under 35 U.S.C. 154(b) by 0 days.

(21) Appl. No.: 09/439,085

(22) Filed: Nov. 12, 1999

(51) Int. Cl.$^7$ .......................... A61K 35/78; A61K 39/385
(52) U.S. Cl. .......................................... 424/195.1
(58) Field of Search .......................................... 424/195.1

(56) References Cited

PUBLICATIONS

Numagami et al. "Attenuation of rat ischemic brain damage by aged garlic extracts: a possible protecting mechnism as antioxidants", Neurochem. Int. 1996, 29(2), 135–143.*
Dalvi et al, "An overview of medicinal and toxic properties of garlic", J. Maharashtra Agric. Univ. 1993, 18(3), 378–81.*
Uchino, Hiroshi, "Nutritional value of S–methlcysteine sulfoxide (SMS) and related sulfur containing amino acids", Nippon Eiseigaku Zasshi, 1973, 28(4), 385–91.*
Sumiyoshi, H., "New pharmacological activities of garlic and its constituents", Nippon Yakurigaku Zasshi. Folia Pharmacologica Japonica, Oct., 1997. Suppl. 1 93p.*
S. Tsuyoshi Ohnishi; *A Possible Beneficial Effect of Aged Garlic Extracts in the Management of Sickle Cell Anemia*, Presented by Inventor, Nov. 1998.
Tamori Miyamoto, M.D.; *Effects of Garlic on Hemograms*; Journal of Machurian Medicine, vol. 22, 379–86, 1935; Abstract.
Shizutoshi Nakagawa, Koji Masamoto, Hiromichi Sumiyoshi, Kazuo Kunihiro and Toru Fawa; *Effects of Raw Garlic Juice and Aged Garlic Extract on Growth of Young Rats and Their Organs After Peroral Administration*; The Journal of Toxicological Sciences, vol. 5, 91–112, 1980.

Sadahiko Kuzutani; *On Effects of Garlic (Allium Scorodoprasum. L.)*; Clinical Pathology and Hematology, vol. 3, No. 11, pp. 1175–1233, 1934.

Seizo Katsunuma; *On Effects of Garlic on Anemia*; Experimental Medicine, vol. 18, pp 442–444, 1932.

Yoshiyasu Hasegawa, Naganori Kikuchi, Yu Kawashima, Shunichi Ishikawa, Yasuhiro Ochiai, Hiroshi Shibata, Kawumasa Shimizu, Muheyuki Nishiyama; *The Clinical Effects of Leopin–5 (LE–5) on Indefinite Complaints in Internal Medicine*; 1984.

Katsugi Nagai, Shizutoshi Nakagawa, Seiko Ohsawa and Hiromi Suemori; *The Effect of Aged Garlic Extract on Experimentally Induced Anemia in Rats*; 1975.

Shizutoshi Nakagawa, Shigeo Kasuga and Hiromichi Matsuura; *Prevention of Liver Damage by Aged Garlic Extract and Its Components in Mice*; Phytotherapy Research, vol. 1., No. 0, 1988.

Winfred C. Wang; *Role of Nutritional Supplement in Sickle Cell Disease*; Journal of Pediatric Hematology/Oncology, vol., 21, No. 3, May/Jun. 1999.

Notification of Transmittal of the International Search Report or the Declaration, Mar. 19, 2001.

* cited by examiner

Primary Examiner—Theodore J. Criares
Assistant Examiner—Jennifer Kim
(74) Attorney, Agent, or Firm—Oblon, Spivak, McClelland, Maier & Neustadt, P.C.

(57) ABSTRACT

This invention deals with a therapeutically effective composition and method for use in ameliorating the effects of sickle cell anemia and sickle cell crisis. The method preferably involves the oral administration, in preferably four doses daily, of an effective amount of a composition containing S-allyl cysteine and S-allylmercapto cysteine (such as aged garlic extract or AGE) with 1 to 10 grams of Vitamin C and between 200 to 1,200 I.U. of vitamin E.

27 Claims, 4 Drawing Sheets

THERAPEUTIC USES OF SPECIALLY PROCESSED GARLIC FOR SICKLE CELL DISEASE

BACKGROUND OF THE INVENTION

1. Field of Invention

The present invention relates to the therapeutic efficacy of a composition containing components found in specially processed garlic for sickle cell anemia patients, particularly, to a method for ameliorating sickle cell anemia and more particularly to a method in which the composition or a specially processed garlic is administered on a daily basis for ameliorating anemia and preventing painful crisis in sickle cell anemia patients.

2. Discussion of the Background

Sickle cell anemia is a genetic disease seen in both African and African-American populations. The patients have a genetically abnormal hemoglobin (called sickle hemoglobin or HbS), which polymerizes at a low oxygen concentration and forms bundles of hemoglobin polymers, thus stretching and deforming red blood cells into a "sickle" shape. This deformation damages the membrane of patients' red blood cells and makes the average life of the red blood cells in the range of 10 to 20 days as opposed to 120 days for normal individuals. As a result, patients suffer from chronic anemia. These damaged red blood cells have a tendency to adhere to the endothelial cells of the blood vessel, neutrophils and platelets, and thus, obstruct blood flow causing frequent painful seizure called "sickle cell crisis," damaging organs and impairing bone joints.

In Africa, one out of fifty persons is estimated to suffer from this disease, and if enough medical assistance is not provided, the average life span of the patients is around 20 years. In the entire African continent, millions of patients are estimated to suffer from this disease. In the United States, about one out of 500 of the African-American population (about 18% of total U.S. population) may suffer from this disease. The total number of sickle cell patients in the United States is estimated to be on the order of 70,000.

There is no known cure for this disease. Currently, the only medication which seems to have some efficacy is an oral administration of hydroxyurea. This compound increases the cellular content of fetal hemoglobin (HbF) which does not polymerize at low oxygen concentration like HbS. However, hydroxyurea has some negative side effects, such as bone marrow suppression, and a life-long administration may not be recommended.

SUMMARY OF THE INVENTION

Accordingly, one object of the present invention is to provide a treatment for those stricken with sickle cell anemia that avoids the side effects of conventional hydroxyurea treatments.

A further object of the present invention is to provide a treatment method for sickle cell anemia patients that helps prevent sickle cell crisis.

These and other objects have been satisfied by the discovery of a method for the treatment of sickle cell anemia comprising administering to a subject in need thereof an effective amount of a composition comprising S-allyl cysteine and S-allylmercapto cysteine to treat and/or prevent anemia and sickle cell crisis.

BRIEF DESCRIPTION OF THE DRAWINGS

Many attendant features of this invention will become readily appreciated as the same becomes better understood by reference to the following detailed description when considered in connection with the accompanying drawings.

DETAILED DESCRIPTION OF THE PREFERRED EMBODIMENTS

Figure 1:
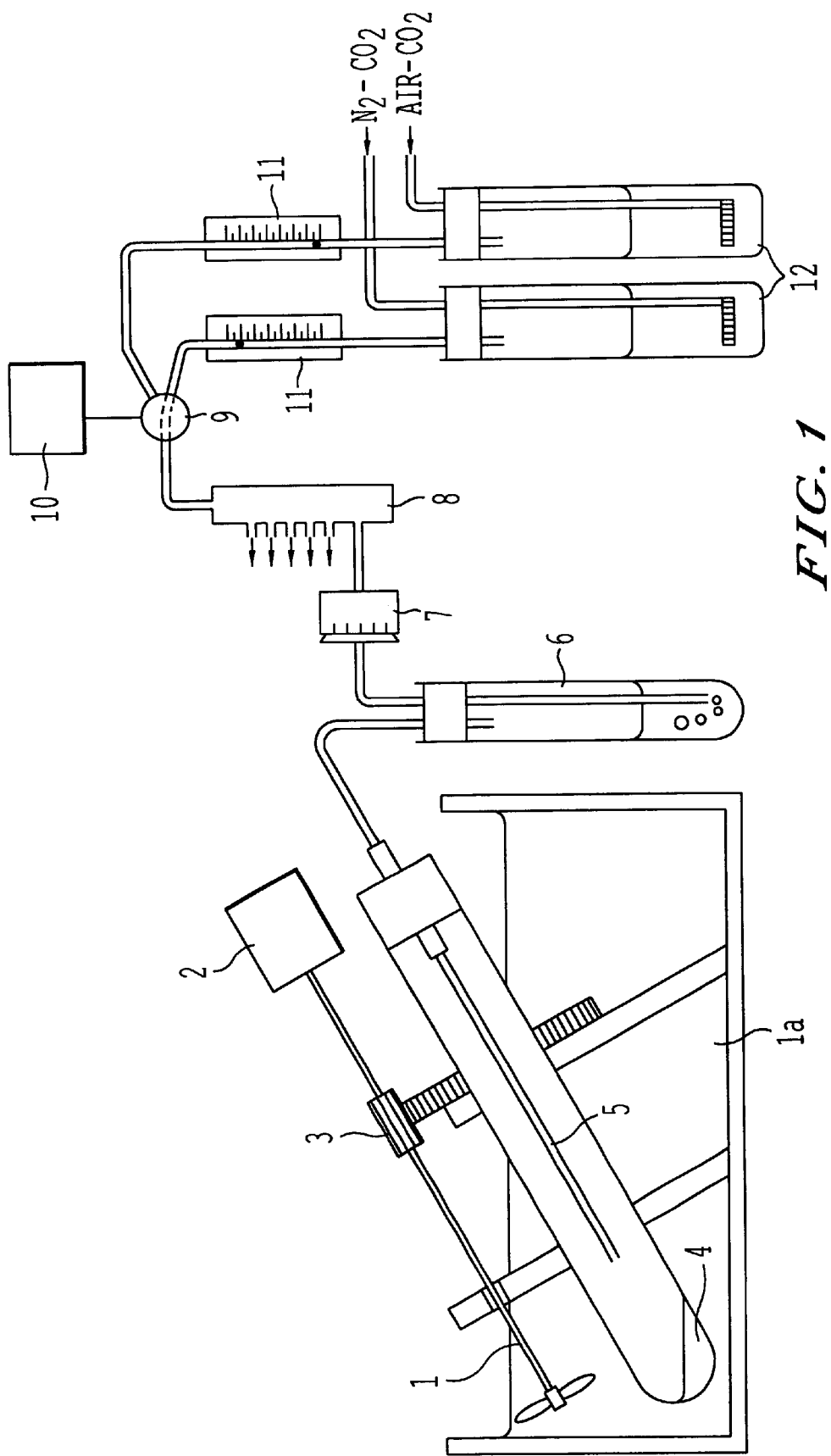
FIG. 1 is a diagrammatic illustration of the apparatus used in the method of preparing dense cells by repeated deoxy-oxy cycling.

The present invention relates to a method for treatment of sickle cell anemia that ameliorates the effects of the associated anemia and helps prevent sickle cell crisis, by administration of a composition comprising S-allyl cysteine and S-allylmercapto cysteine to a patient in need thereof in an amount sufficient to prevent sickle cell crisis.

The composition comprising S-allyl cysteine and S-allylmercapto cysteine may also contain other components. One preferred additional component is N-alpha-(1-deoxy-Dfructos-1-yl)-L-arginine (fructosyl arginine). A most preferred embodiment uses a garlic extract containing these three components. Raw garlic does not contain sufficient levels of these three materials. It is only upon processing the garlic that the levels of SAC and SAMC are increased to the effective level. The garlic extract can be prepared in any fashion sufficient to increase the levels of SAC and SAMC. Most preferably, the garlic extract is an aged garlic extract (AGE) prepared by the method described in the Example below and as described in U.S. patent application Ser. No. 09/133,267, filed Aug. 13, 1998, the contents of which are hereby incorporated by reference. Additionally, AGE is commercially available under the trade name KYOLIC®, from Wakunaga of America Co., Ltd. in Mission Viejo, Calif. or under the tradename KYOLEOPIN®, from Wakunaga Pharmaceutical of Japan.

The composition of the present invention can be administered in any suitable orally administerable form. Suitable forms include powder, tablet, capsule, solutions, etc. The preparation of such administration forms is well known in the art and can also include conventional auxiliaries or excipients. When the composition of the present invention is administered as a liquid form, the amount of the composition in solution is sufficient to provide the required daily dosage in a volume of 1 to 40 mL/day.

Because the present composition, particularly AGE, does not cause significant negative side effects, it can be administered indefinitely to the sickle cell patient. Preferably, treatment is continued for the lifetime of the patient.

In practicing the method of the present invention, the composition, such as AGE, can be administered alone, or together with other antioxidants and/or supplements. When administered with other antioxidants, the composition and other antioxidants can be formulated together for administration or can be administered concurrently as separate dosage forms.

Suitable other antioxidants for administration with the present composition include, but are not limited to, Vitamin A, Vitamin C, Vitamin E, β-carotene, selenium and other conventional antioxidants. Preferred among the antioxidants are Vitamin C and Vitamin E.

The dosage of the present composition can be administered once a day or in a multidose per day regimen. The total daily dosage is a dosage sufficient to prevent sickle cell crisis. With AGE, this is preferably from 1 to 10 grams, more preferably from 1 to 6 grams, most preferably from 2 to 4 grams. The dosage can be divided into equal or unequal administrations during the day, preferably into four equal doses. If unequal dosages are used, the dosages should be adjusted to provide an approximately equal level of the composition's active ingredients in the bloodstream throughout the day, with larger dosages being provided when the time between doses is higher and smaller dosages being provided when the time between doses is shorter.

When administered in conjunction with Vitamin C or Vitamin E the corresponding amounts of Vitamin C range from 1–10 g after day, preferably 2 to 7 g per day and the amount of Vitamin E ranges from 200–1,200 I.U. per day, preferably from 400 to 800 I.U. per day.

The present composition and other antioxidants can be administered together in all doses given or can be varied with the present composition/Vitamin C at certain times of the day and the present composition/Vitamin E in the remaining doses for the day.

The inventor has found that typical "sickle" shaped cells can be prepared in vitro by exposing sickle red blood cells to repeated deoxygenation-oxygenation (D-O cycling), and that these of elongated "sickle" shaped cells had an elevated density (Ohnishi, S.T., Horiuchi, K. Y. and Horiuchi, K., Pharmacology 32:248–256, 1986). It was also found that if D-O cycling was continued for several hours, the density further increased leading to the formation of permanently deformed cells known as irreversibly sickled cells (Ohnihsi, S. T. British J of Haematology. 55:665–671, 1983).

It has been known that a certain percentage of red blood cells in sickle cell anemia patients are dehydrated and have an elevated density and that they seem to trigger sickle cell crisis (Ballas, S. K. and Smith, E. D. Blood 79:2154–2163, 1992; Fabrey, M. E., Benjamin, L., Lawrence, C. and Nagel, R. L. Blood 64:559–563, 1984). Therefore, the present invention sought to find compounds which could inhibit the formation of dehydrated dense cells in vivo. Such compounds could prevent sickle cell crisis. This is exactly the reason why this invention is important.

As R. P. Hebel (J. Lab. Clin. Med. 107:401–404, 1986) and Rice-Evans, C., Omorphos, S. C. and Baysal, E (Biochem. J. 237:265 269, 1986) proposed, cycling of hemoglobin and methemoglobin produces superoxide anions, which by superoxide dismutase (SOD) or spontaneously are dismuted to produce hydrogen peroxide. Superoxide and hydrogen peroxide are catalyzed by membrane-bound hemichrome and/or compartmented iron to produce hydroxyl radicals. All these reactive oxygen species (ROS) would attack membrane lipid and proteins to enhance calcium entry and potassium exit (with water following) to form dense cells.

Interestingly, raw garlic has been found to be a possible cause of conventional anemia causing reduced red cell count and reduced hemoglobin, as well as increased white cell count during the period of administration, which corrects to normal levels upon cessation of administration of the raw garlic. S. Katsunuma, *Exper. Med.*, 18, 442–444 (1932) and S. Kuzutani, *Clin. Path. and Hemat.*, 3, 1175–1233 (1934). AGE, on the other hand, has been shown to not cause the same reduction of red cell count and hemoglobin. S. Nakagawa et al, *J. Toxic. Sci.*, 5, 91–112 (1980). This is believed to be due to the removal of most of the oil-soluble sulfur containing compounds from the raw garlic during the extraction/processing step.

A most preferred embodiment, AGE has a strong antioxidant activity, and therefore, it could protect the membrane of red blood cells and other tissues of the patients from oxidative injury.

Although the present inventor does not wish to be bound to any particular mechanism of action, it is believed that the present composition, particularly AGE, seems to have the following beneficial effects: (1) AGE scavenges ROS in the aqueous phase (both in plasma and inside red blood cells) thus protecting the red cell membrane and other tissues; (2) AGE not only scavenges ROS in the aqueous phase, but also increases the levels of superoxide dismutase, glutathione, glutathione S-transferase and glutathione peroxidase mechanisms (Geng, Z. and Lau B. *Phytother. Res.* 11:54–56, 1997; Hatono, S., Jimenez, A. and Wargovich, M. *Carcinogenesis* 17: 1041–1044, 1996; Liu, J. and Milner, J. *FASEB J.* 6:3230, 1992; Wei, Z. and Lau, B. H. S. *Nutr. Res.* 18:6170, 1998), all of which are important cellular defense components. Other antioxidants, such as vitamin C and vitamin E, enhance the protecting action of the present composition, particularly that of AGE, in sickle cell anemia patients.

Referring to FIG. 1, there is shown an apparatus for preparing dense cells in vitro by repeated deoxy-oxy (D-O) cycling. The apparatus includes a stirring device 1 for the thermostatic bath 1a. A motor 2 drives the stirrer for the bath through a gear system 3. The rotating test tube is shown at 4, rotating at about 27 rpm. Positioned within the test tube 4 is a plastic tubing such as Teflon tubing. Individual humidifier 6 is shown receiving the flow from the flow control valve 7, the latter connected to manifold 8. Flow control valve 7 is used to adjust the flow rate and cooperates with flow switch 9 which functions as an on-off valve. The system also includes a timer 10, flow meters 11 and a humidifier for each gas line. As shown, one gas is a mixture of nitrogen and carbon dioxide and the other is a mixture of air and carbon dioxide.

Figures 2A, 2B, 2C, 2D, 2E:
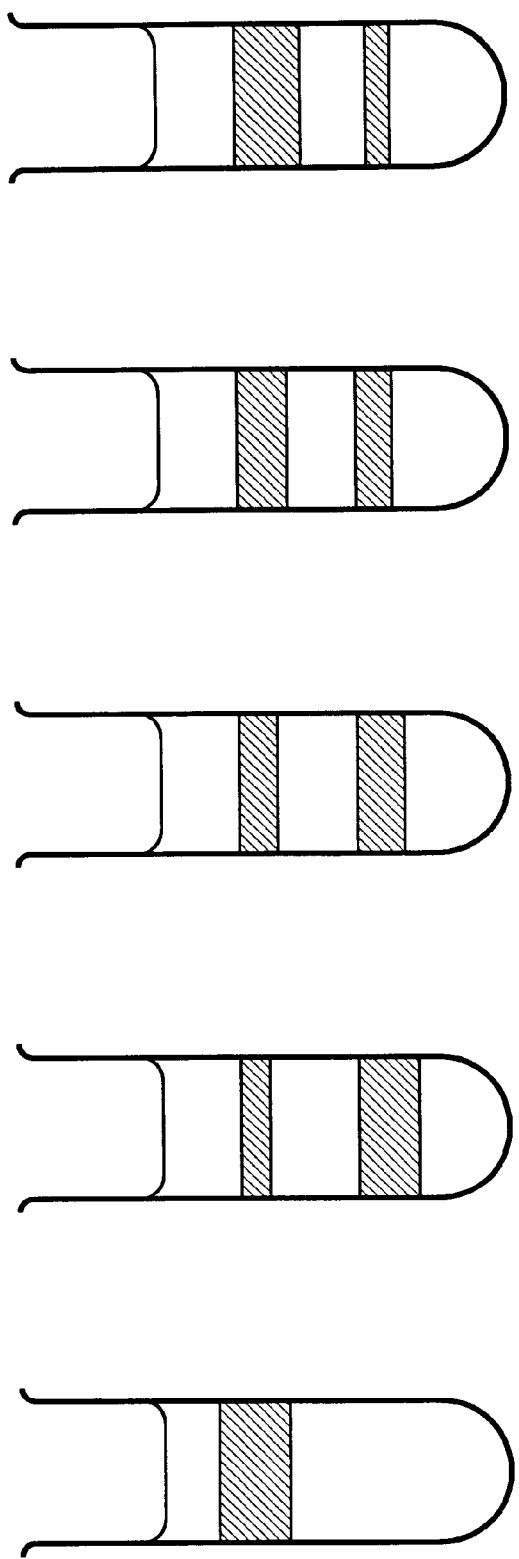
FIGS. 2A–2E are illustrations of the results of overlayering reversible sickle cells with various materials.

Referring now to FIG. 2, RSC (reversible sickling cells) were overlayered on the preformed density gradient solution and spun at 2,500 rpm for 10 minutes. FIG. 2A shows diagrammatically the RSC which were exposed to straight deoxygenation for one hour to form only the top layer (lighter density). FIG. 2B shows diagrammatically RSC which were exposed to repeated Deoxy-Oxy cycling for one hour to form the top layer and bottom layer (higher density). If specially processed garlic (AGE), to be described, was added to the RSC suspension 30 minutes prior to the start of Deoxy-Oxy cycling, the amount of red blood cells in the bottom layer decreased. The concentration of AGE added to the RSC suspension were, FIG. 2C 3 mg/ml, FIG. 2D 6 mg/ml and FIG. 2E 20 mg/ml, respectively.

Figure 3A:
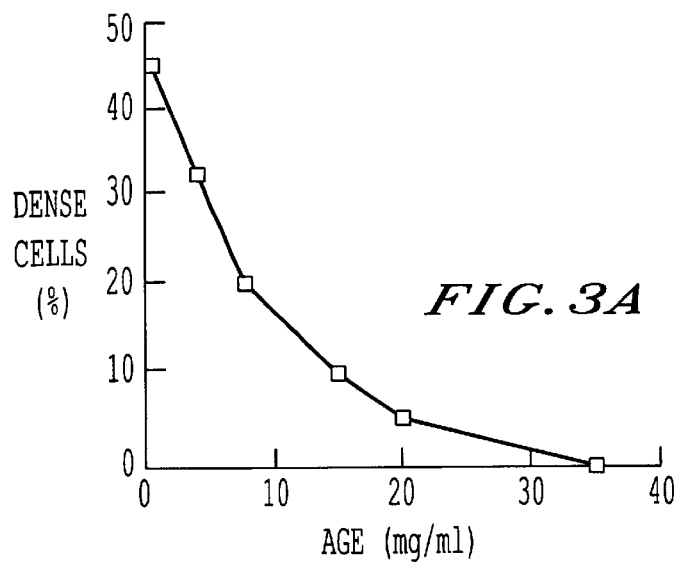
FIGS. 3A–3C are graphs illustrating the dose responsive relationship of the inhibition of dense cell formation of various materials.
Figure 3B:
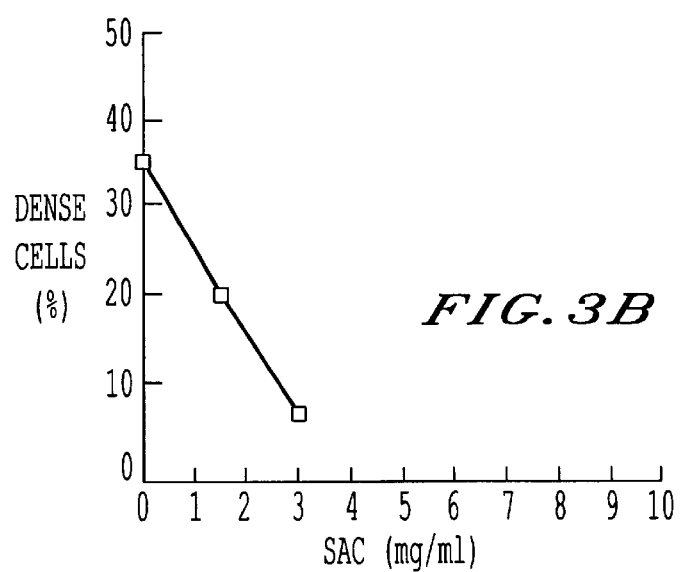
Figure 3C:
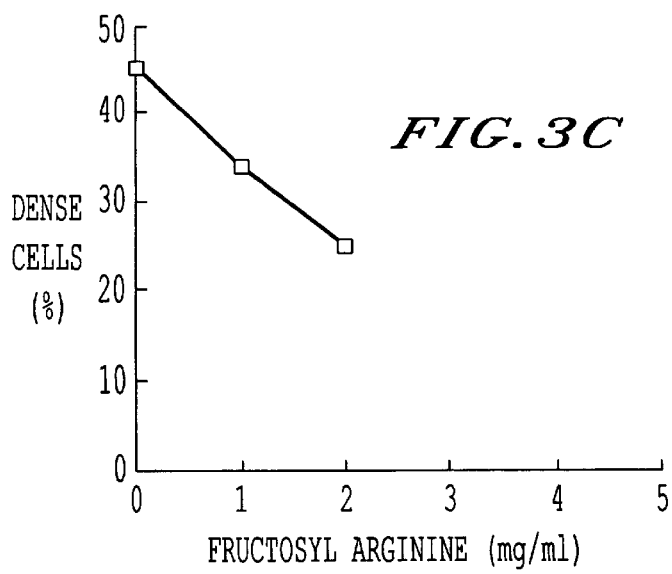

In FIG. 3, the dose response relationship of the inhibition of dense cell formation by (A) AGE, (B) SAC and (C) fructosyl arginine are illustrated. Each chemical was added to the sickle cell suspensions 30 minutes prior to the start of D-O cycling.

Figure 4:
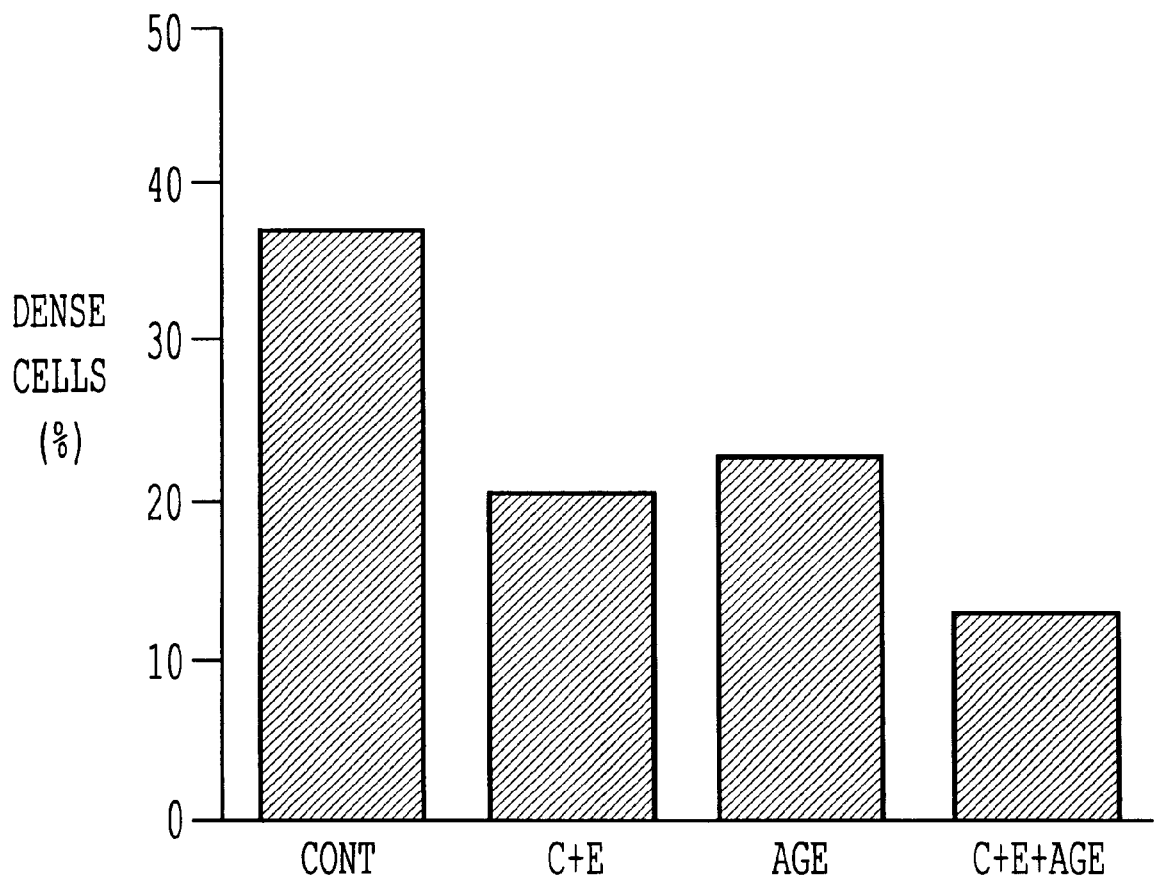
FIG. 4 is a plot indicating the in vitro dense cell formation is inhibited by the sera taken from a volunteer who has taken various nutrients for several days.

FIG. 4 illustrates inhibition of in vitro dense cell formation by plasma taken from a volunteer who had orally taken antioxidants. From left to right of FIG. 4: (A) Control (no compound); (B) 4 g vitamin C+800 I.U. vitamin E (daily); (C) 6 g AGE (daily); and (D) the combination thereof. Sickle red blood cells were incubated in these plasma 60 minutes prior to the start of D-O cycling.

Examples of this invention are set forth below. However, it is to be understood that these examples are given by way of illustration only and are not to be construed as limiting the invention either in spirit or in scope, as many modifications both in doses and methods could be possible to those skilled in the art.

EXAMPLES
Experimental Design and Results

EXAMPLE 1
Inhibition of Dense Cell Formation in in vitro Experiments
Solutions The reaction medium consists of: 109 mM NaCl, 6 mM KCl, 5 mM $CaCl_2$, 1.2 mM $MgSO_4$, 20 mM HEPES buffer, 25 mM $NaHCO_3$, 2.4 mM $Na_2HPO_4$, 1 mM adenine, 1 mM inosine, 10 mM glucose, 0.05 mg/ml each of penicillin and streptomycin and 2% bovine serum albumin. The osmolarity of the medium was adjusted to 290 mOsm/kg using a freezing point osmometer and the pH was adjusted to 7.4 after equilibrated with 95% air/5% $CO_2$. Since the sickle cell is pH-sensitive, and since the addition of testing compounds tends to change pH, the pH of the reaction medium was always re-adjusted to 7.4±0.01 under gas flow of 95% air/5% $CO_2$ after the addition of any testing compounds.

A Percoll-stock solution was prepared as follows. To a 100 ml Percoll solution (Pharmacia Biotech, Pistcataway, N.J.)., 117 mM NaCl, 20 mM $KH_2PO_4$, 0.005 g each of penicillin and streptomycin were added. The pH was adjusted to 7.4. The osmotic pressure of this solution was adjusted to 290 mOsm/kg. The density as determined with a picnometer was 1.1365.

A diatrizoic acid (Sigma Chemicals, St. Louis, Mo.) stock solution was prepared as follows: To 80 ml water, 115 mM diatrizoic acid was added. Then, 8 ml of 2M NaOH was added to solubilize the compound. Then, 20 mM $KH_2PO_4$, was added and the pH adjusted to 7.4 with 1M HCl. Finally, the volume of the solution was made to 100 ml and the osmolarity was adjusted to 290 mOsm/kg. The density was 1.0475. A density gradient solution with the density of 1.104 was prepared by mixing one volume of the percoll stock solution and 0.575 volume of the diatrizoic acid stock solution.

Nutritional Compounds Used in in vitro studies

Specially processed garlic (AGE) and its two components, namely, S-allyl cysteine (SAC) and N-alpha-(1-deoxy-D-fructos-1-yl)-L-arginine (fructosyl arginine) were prepared by Wakunaga Pharmaceuticals (Mission Viejo, Calif.). Basically, AGE is a special product, described above, extracted from garlic which has been grown organically and aged under controlled conditions. AGE contains S-allyl cysteine and S-allyl mercaptocysteine, the latter reported to be potent antioxidants. AGE is to be distinguished from ordinary garlic or garlic flavoring products or heat distilled oils and heat dried powders derived from garlic.

AGE is rich in water soluble compounds and contains small amounts of oil-soluble compounds. At least nine oil-soluble organosulfur compounds have been identified, including allyl sulfide, allyl disulfide (diallyl sulfide), allyl trisulfide, allyl methyl sulfide, allyl methyl disulfide, allyl methyl trisulfide, methyl disulfide, methyl trisulfide and ethyl 2-propenesulfinate. These compounds are in addition to the S-allyl cysteine and S-allyl mercaptocysteine materials already mentioned.

Since AGE contained a small amount of alcohol, it was dried under the vacuum and suspended with the reaction medium used for the experiments and pH adjusted to 7.4 after equilibrating with 95% N2/5% $CO_2$. Both SAC and fructosyl arginine were dissolved into the reaction medium to a concentration of 20 mg/ml and the pH adjusted to 7.4 under 95% N2/5% $CO_2$. These compounds were stored at −80° C.

Blood

For in vitro tests, blood was obtained from adult sickle cell patients (using citrate-phosphate-dextrose-adenine as an anticoagulant) whose hemoglobin F content is less than 1% and whose content of irreversibly sickled cells is less than 10%. The blood could be used for several days as long as the airspace of the container was equilibrated with 95% air/5% $CO_2$ and the container was gently tumbled (1 to 2 rpm) at 4° C.

Density Gradient Separation of Blood

One ml of the density gradient solution (density=1.104) was poured into 10×75 mm glass test tube, and was inserted into a plastic centrifuge tube (i.d. 12.5 mm, length 100 mm) to which 2.5 ml water had been added to help supporting the glass test tube. Then, the tubes were spun at 12,000 rpm for 5 min. by which a density gradient was automatically formed. Then, 100 μl of blood was overlayered on top of the pre-formed density gradient, and was spun for 10 minutes at 2,500 rpm using a low speed centrifuge with a swing rotor.

The red blood cells were separated into two layers, namely, a light fraction with the density lighter than 1.104 (top layer) and a heavy dense cell fraction with the density higher than 1.104 (bottom layer). Then, the red blood cells in the top layer, which consists of reversibly sickling cells (RSC), were collected, washed with the reaction medium, resuspended in the same medium, and used for the experiments.

Deoxy-Oxy Cycling (D-O Cycling) Method

FIG. 1 show the schematic illustration of the apparatus used in the Deoxy-Oxy Cycling method. Washed RSC were suspended in the reaction medium to make the hematocrit value of 1–2%. Then, 1 ml each of this suspension was added to 8 test tubes all of which were rotated at 27 rpm by a motor-gear mechanism in a thermostatic bath at 37±0.2° C. which has been described. Using a timer, two gas mixtures (95% N2/5% $CO_2$ and 95% air/5% $CO_2$) alternately flushes the inside of each tube at the flow rate of 30 ml/min/each tube. The period of cycling was 10 min 40 sec for N2/CO2 and 1 min 20 sec for air/$CO_2$.

Density Gradient Separation of Dense Cells

As described above, 1 ml of the density gradient solution with the density of 1.110 was spun at 12,000 rpm for 5 min to form gradient density. Then, 100 μl of a blood suspension was overlayered on top of the pre-formed density gradient, and was span for 10 minutes at 2,500 rpm using a low speed centrifuge with a swing rotor. When the suspension of RSC was exposed to only oxygenation (air-CO2) or deoxygenation (air-NO2), only the top layer was observed indicating that the density did not change. However, if the suspension of RSC was exposed to repeated D-O cycling, two layers, top and bottom layers, were formed (Ohnishi, S. T. British J of Haematology. 55:665–671, 1983). The bottom layer had a higher density, and is called herein Dense cells." Each layer was carefully collected, wash-centrifuged once with the reaction medium, and the cells were hemolyzed with a solution containing 5 mM sodium phosphate buffer (pH 7.4), 1 mM EDTA and 0.3% Brij 35. From the hemoglobin content of each layer as measured spectrophotometrically, the percentage of red cells in the bottom layer was calculated (Ohnishi, S. T., Horiuchi, K. Y. and Horiuchi, K. Biochim. Biophys. Acta 886:119–129, 1986).

FIG. 2. shows a result of density gradient centrifugation where different concentrations of AGE (from 0 to 20 mg/ml) were added to RSC suspensions and incubated for 30 minutes prior to the start of D-O cycling, which lasted for one hour. The percentage of bottom layer (dense cells) decreased when the concentration of AGE increased. FIG. 3 shows that AGE and its components, SAC and fructosyl arginine, inhibited dense cell formation in a dose-response manner.

EXAMPLE 2
Inhibition of Dense Cell Formation in ex vivo Experiments
Nutritional Compounds Used in ex vivo Studies Kyolic capsules (containing 300 mg of AGE), Vitamin C tablets (1000 mg/tablet) and vitamin E soft gels (200 I.U. d-alpha-tocopherol per gel) were purchased from a health food store.

Ex vivo Method of Testing the Efficacy of Orally Taken Antioxidants

This method involves the intake of antioxidants by a healthy volunteer (not a sickle cell patient) who has type AB blood. The advantage of type AB blood is that it can accept any type of red blood cells. After several days of orally taking particular nutritional supplements, blood was withdrawn and the plasma separated by centrifugation of 2500 rpm×10 minutes. Using the plasma as a Reaction medium," the D-O cycling of reversible sickle cells were performed. The inhibition of the formation of dense cells by the volunteer's serum in this "ex vivo" experiments is related to the inhibition of "in vivo" formation of dense cells when patients orally take the same nutritional supplements.

The following combination of nutritional supplements were tested: (A) No supplements; (B) Intake of daily doses of 4 g vitamin C+800 I.U. vitamin E; (C) 6 g AGE; and (D) 4 g vitamin E plus between 1 and 6 g AGE and preferably 6 grams of AGE. The daily doses were split into 4 parts, and each was taken orally 4 times a day: after each meal and at bed time.

FIG. 4 shows the results of this ex vivo experiments. As seen in the figure, AGE inhibited dense cell formation almost to the same degree as that by a mixture of two antioxidants, vitamin C and vitamin E. Further, by the "Cocktail" which contained all compounds, namely, AGE, vitamin C and vitamin E, we observed the greatest inhibitory activity. These results strongly suggest that AGE would have beneficial effects on sickle cell patients, either by itself or by combining with other antioxidants.

It will be apparent from the above detailed description that there are many variations in the present invention and thee same are deemed to be subject to this invention as set forth in the appended claims.

What is claimed is:

1. A method for the treatment of sickle cell disease comprising:
   administering to a subject in need thereof, an effective amount of a composition comprising S-allyl cysteine and S-allylmercapto cysteine.

2. The method of claim 1, wherein said composition further comprises fructosyl arginine.

3. The method of claim 1, wherein said administering step further comprises administration of one or more additional antioxidants with said composition.

4. The method of claim 3, wherein said composition and said one or more additional antioxidants are administered concurrently in separate doses.

5. The method of claim 3, wherein said composition and said one or more additional antioxidants are administered as a single dosage mixture.

6. The method of claim 1, wherein said administering step is performed in a single dose per day.

7. The method of claim 1, wherein said administering step is performed in multiple equal or unequal doses per day.

8. The method of claim 7, wherein said multiple doses per day are four doses per day.

9. The method of claim 8, wherein said four doses per day are from equal doses per day.

10. The method of claim 8, wherein said four doses per day are four unequal doses per day in amounts effective to maintain a sufficient blood level of S-allyl cysteine and S-allylmercapto cysteine.

11. The method of claim 3, wherein said one or more additional antioxidants comprise a member selected from the group consisting of Vitamin A, Vitamin C, Vitamin E, β-carotene, selenium, and mixtures thereof.

12. The method of claim 11, wherein said one or more additional antioxidants are a member selected from the group consisting of Vitamin C, Vitamin E, and mixtures thereof.

13. A method for the treatment of sickle cell disease comprising:
   administering to a subject in need thereof, an effective amount of a composition comprising an aged garlic extract (AGE).

14. The method of claim 13, wherein said administering step further comprises administration of one or more additional antioxidants with said aged garlic extract.

15. The method of claim 14, wherein said age garlic extract and said one or more additional antioxidants are administered concurrently in separate doses.

16. The method of claim 14, wherein said aged garlic extract and said one or more additional antioxidants are administered as a single dosage mixture.

17. The method of claim 13, wherein said administering step is performed in a single dose per day.

18. The method of claim 13, wherein said administering step is performed in multiple equal or unequal doses per day.

19. The method of claim 18, wherein said multiple doses per day are four doses per day.

20. The method of claim 19, wherein said four doses per day are four equal doses per day.

21. The method of claim 19, wherein said four doses per day are four unequal doses per day in amounts effective to maintain a sufficient blood level of aged garlic extract.

22. The method of claim 14, wherein said one or more additional antioxidants comprise a member selected from the group consisting of Vitamin A, Vitamin C, Vitamin E, β-carotene, selenium, and mixtures thereof.

23. The method of claim 22, wherein said one or more additional antioxidants are a member selected from the group consisting of Vitamin C, Vitamin E, and mixtures thereof.

24. The method of claim 23, wherein said aged garlic extract is present in an amount sufficient to provide a daily dose of from 1 to 10 g/day, said Vitamin C is present in an amount sufficient to provide a daily dose of from 1 to 10 g/day and said Vitamin E is present in an amount sufficient to provide a daily dose of from 200 to 1,200 I.U./day.

25. The method of claim 24, wherein said aged garlic extract is in liquid solution and is administered in an amount of 1 to 40 mL/day.

26. The method of claim 13, wherein said aged garlic extract is administered in an amount of from 1 to 10 g/day.

27. The method of claim 26, wherein said aged garlic extract is in liquid solution and is administered in an amount of 1 to 40 mL/day.

* * * * *